(12) United States Patent
Asselin et al.

(10) Patent No.: US 10,168,294 B2
(45) Date of Patent: Jan. 1, 2019

(54) CAP INSPECTION AND MANUFACTURE

(71) Applicant: MMC PACKAGING EQUIPMENT LTD, Laval (CA)

(72) Inventors: Yannick Asselin, Terrebonne (CA); Marcel Bélanger, Ste-Julie (CA); Yves Lemelin, Saint-Jérôme (CA); Charles St-Hilaire, Oka (CA)

(73) Assignee: MMC PACKAGING EQUIPMENT LTD, Laval, QC (CA)

( * ) Notice: Subject to any disclaimer, the term of this patent is extended or adjusted under 35 U.S.C. 154(b) by 0 days.

(21) Appl. No.: 15/702,139

(22) Filed: Sep. 12, 2017

(65) Prior Publication Data

US 2018/0100824 A1    Apr. 12, 2018

Related U.S. Application Data

(63) Continuation of application No. PCT/CA2016/051178, filed on Oct. 7, 2016.

(51) Int. Cl.
| | |
|---|---|
| G01N 27/20 | (2006.01) |
| G01M 3/40 | (2006.01) |
| B07C 5/344 | (2006.01) |
| B07C 5/36 | (2006.01) |

(52) U.S. Cl.
CPC .......... *G01N 27/205* (2013.01); *B07C 5/344* (2013.01); *B07C 5/365* (2013.01); *G01M 3/40* (2013.01)

(58) Field of Classification Search
CPC .......... B07C 5/02; B07C 5/122; B07C 5/124; B07C 5/128; B07C 5/3404; B07C 5/344; G01N 27/20; G01N 27/205; G01N 27/22; G01N 27/24; G01M 3/40

USPC .................. 209/522–524, 526, 530
See application file for complete search history.

(56) References Cited

U.S. PATENT DOCUMENTS

| | | | |
|---|---|---|---|
| 3,395,573 A * | 8/1968 | Baker .................. | B07C 5/3408 209/530 |
| 3,465,242 A | 9/1969 | Gruetzmacher et al. | |
| 3,543,924 A * | 12/1970 | Sullivan .................... | B07C 5/34 209/572 |
| 3,700,101 A * | 10/1972 | Ference ................ | G01M 3/366 209/549 |
| 3,717,248 A * | 2/1973 | Scribner ............... | B07C 5/3404 209/523 |
| 4,125,805 A | 11/1978 | Nagamatsu | |
| 4,431,961 A | 2/1984 | Kakumoto | |
| 5,510,718 A * | 4/1996 | Enderby .................. | G01M 3/40 324/536 |
| 6,009,744 A | 1/2000 | Kovalchick | |
| 6,025,567 A | 2/2000 | Brooks | |
| 6,473,169 B1 * | 10/2002 | Dawley ............... | G01M 3/3263 250/223 B |

(Continued)

FOREIGN PATENT DOCUMENTS

| | | |
|---|---|---|
| DE | 102013014473 A1 | 3/2015 |
| EP | 2365309 B1 | 8/2015 |

(Continued)

*Primary Examiner* — Joseph C Rodriguez
(74) *Attorney, Agent, or Firm* — Anglehart et al.

(57) ABSTRACT

An inspection apparatus for testing of objects synchronizes a spark test wheel having probe fingers with a transportation unit on which spaced objects to be spark tested are placed. The probe fingers are arranged conically when the transportation unit is a turret.

19 Claims, 6 Drawing Sheets

(56) References Cited

U.S. PATENT DOCUMENTS

| | | |
|---|---|---|
| 6,634,216 B1 | 10/2003 | Yasumoto |
| 7,038,464 B2 | 5/2006 | Holzer |
| 8,018,236 B2 * | 9/2011 | Formenti ............. G01R 31/025 |
| | | 264/406 |
| 8,973,425 B2 * | 3/2015 | Dzikowicz ............. G01M 3/40 |
| | | 73/40 |
| 2018/0100829 A1 * | 4/2018 | Schonhoff ............. G01N 27/61 |

FOREIGN PATENT DOCUMENTS

| | | |
|---|---|---|
| JP | 2004-099304 A | 4/2004 |
| JP | 2002-148241 A | 5/2005 |
| WO | WO 95/09351 A1 | 4/1995 |
| WO | WO 2012/017360 A1 | 2/2012 |
| WO | WO 2013/104365 A1 | 7/2013 |

* cited by examiner

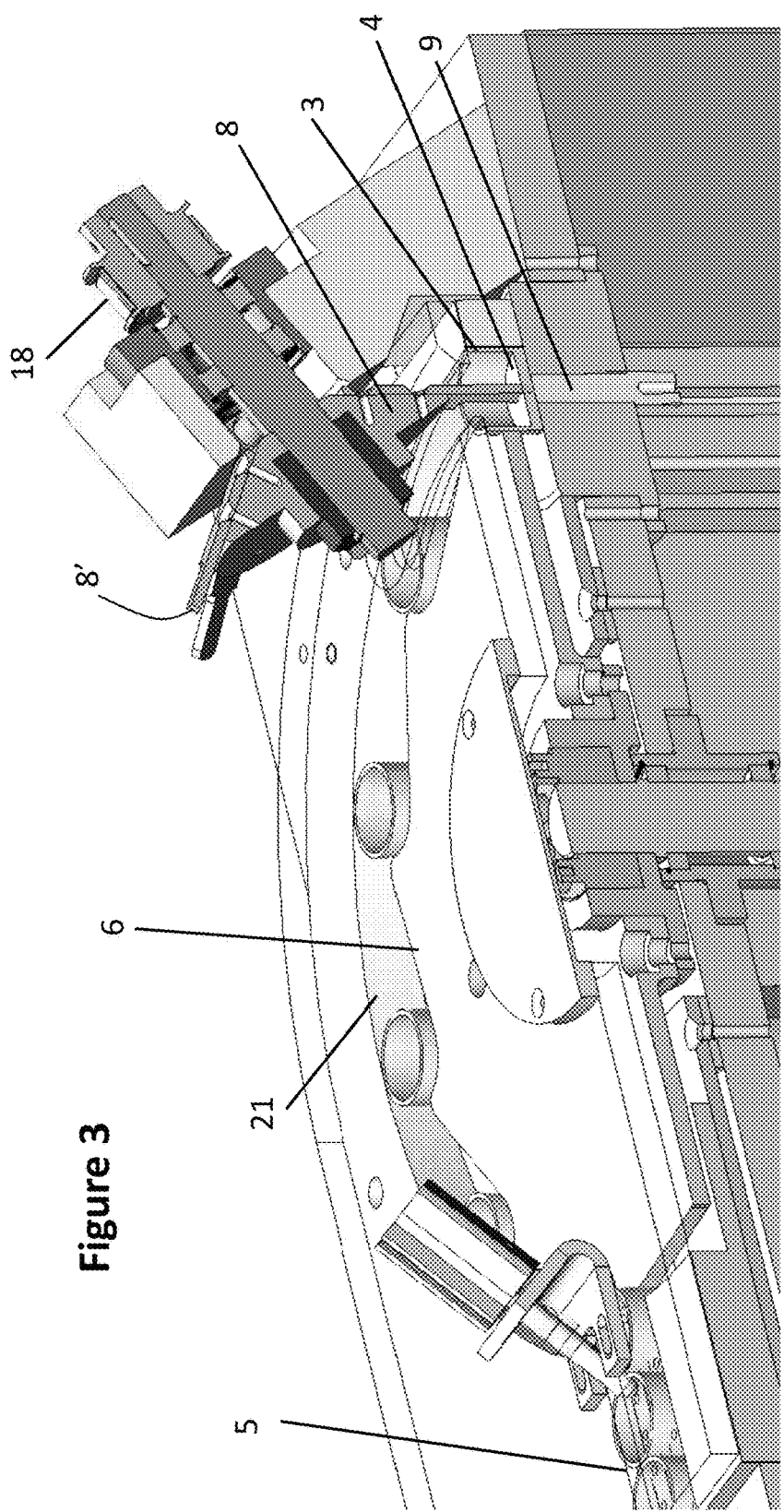

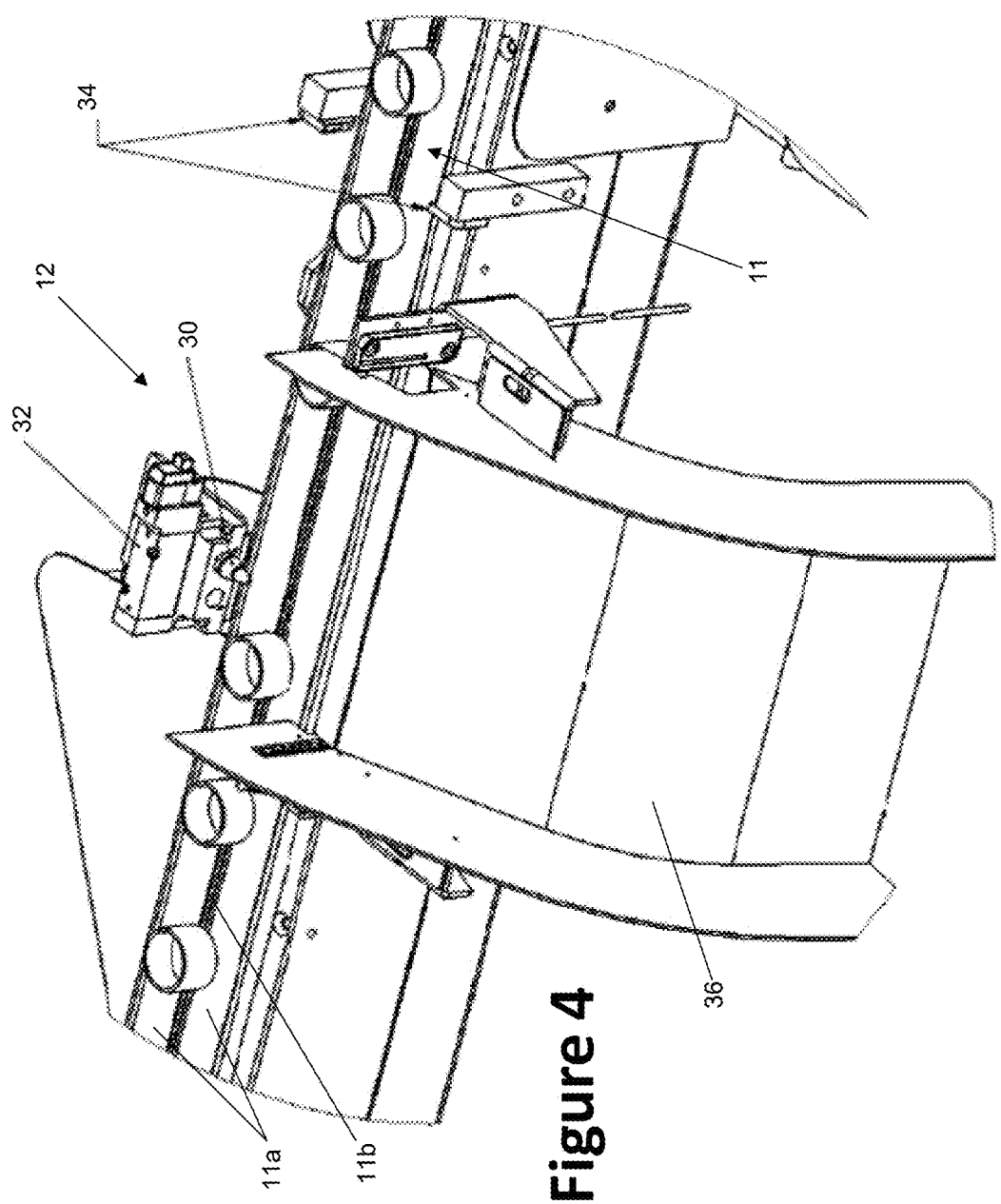

CAP INSPECTION AND MANUFACTURE

This application is a continuation of PCT/CA2016/051178 filed Oct. 7, 2016.

TECHNICAL FIELD

This patent application relates to the field of cap inspection and manufacture, and more particularly it relates to automated spark inspection of plastic caps for bottles and the production of caps and/or capped containers or bottles.

BACKGROUND

The present technology refers to a method for detecting the presence of micro-holes and cracks in caps (or containers) at high speeds surpassing thousands caps per minute and an apparatus for enacting the aforementioned method, as described in their respective independent claims.

Spark inspection of injection molded bottle caps is known to be an effective way of controlling the quality of the caps by ensuring that they are free of micro tears or micro holes that can result from the molding process, particularly at high speed. One electrode is inserted into an inside of the cap while another is positioned on an outside of the cap, and high voltage is applied to the electrodes. If a spark is able to pass through the plastic, insulating cap, then there is a micro hole or tear in the cap. Such defects detected by spark testing are not efficiently detected by optical testing or by pressure testing methods.

Container cap manufacturing can involve processing using turret-based machinery. When a spark test unit is combined with such machinery, a spark test line or a separate spark test wheel is added to the equipment.

Spark testing requires a voltage that is proportional to the gap between the electrodes. To avoid having to use higher voltages, it is best to minimize the gap, to the point of contact between the electrodes and the cap. When doing so, high speed conveyance of the caps being tested becomes a challenge as the contact between the electrodes and the cap disrupts the flow.

It is known to perform a spark test using a star or pocket wheel fit with a spark test electrode associated with each cavity. The pocket wheel contains a plurality of cavities over which a plurality of mechanical vertical plungers bearing electrodes is installed. As the wheel rotates, the mechanical plungers insert the electrodes inside the caps being tested and the latter proceed to accomplish the high voltage spark testing. After the test is accomplished, the electrodes are lifted out of the caps. This system allows pressure to be exerted between the test electrode inserted into the cap cavity and the bottom of the cap. However this system requires a moving mechanism for each cavity of the pocket wheel. This requires additional floor space and increases the need for maintenance.

Some testing systems use a conveyor system that feeds caps to be tested with their interior side facing upwards with an electrode probe wheel having a number of probe "fingers" that rotate to move into and out of the cavities of the caps being conveyed. In these testing systems, the electrode probe wheel can turn as a result of contact with the conveyed caps or the electrode probe wheel can be driven by a motor turning independently of the conveyance of the caps. The tips of the probe fingers can be shaped to make good contact with the bottom of the caps.

German patent application publication DE102013014473 describes a belt conveyor with a vacuum unit in the middle and contains a spark testing unit. The testing unit takes the form of a rotating round-headed detecting device with probe fingers which comes in contact with vessels (i.e. caps) in order to apply a high voltage. An opposed stationary electrode is arranged between the vacuum belts, and the spark test thereby determines the presence of micro-holes. The vacuum belt conveyor provides the initial drive for the caps. The spark test probe wheel, whose probe fingers also makes contact with the inner sidewalls of the caps, sets a spacing between the caps fed by an input queue with the caps in contact with each other. The spark test is performed on each cap and output caps are spaced from each other by the vacuum belt. Providing a physical space between the caps to allow for a rejection of faulty vessels by the apparatus.

This approach can work well at high speed and provides a precise rejection of faulty caps or vessels. However, this approach does not allow for significant pressure to be exerted by the electrodes against the cap or container being tested, and thus requires a higher testing voltage.

Spark inspection may also be integrated into a "larger" automation solution for the manufacturing of plastic caps, such as slitting and folding of tamper evident band. In such a configuration, the current art requires that the spark testing be conducted on a conveying system that is outside of the overall equipment footprint.

SUMMARY

Applicant has discovered that setting a fixed spacing between the conveyed parts to be spark tested and synchronizing a spark test probe wheel with the fixed-spaced conveyed parts allows for spark inspection of the parts to be performed at much higher speed than the prior art with a reduction in the gap between the electrodes to operate at lower test voltage and with the reliability of a single spark test probe wheel for the test line.

Applicant has further discovered that spark testing can be performed within the confines of an existing turret-based conveyor of a turret-based manufacturing equipment using a frustoconical spark test probe. Thus, a method and an apparatus are provided for detecting the presence of micro-holes in caps which uses a frustoconical testing device having a plurality of probe fingers which allows for a rapid testing of caps conveyed by a circular conveyor, such as a turret or a pocket wheel.

In some embodiments, an inspection apparatus for testing of objects synchronizes a spark test wheel having probe fingers with a test area conveyor on which spaced objects to be spark tested are placed. The probe fingers can be arranged conically when the test area conveyor is a turret.

BRIEF DESCRIPTION OF THE DRAWINGS

The invention will be better understood by way of the following detailed description of embodiments of the invention with reference to the appended drawings, in which:

FIG. 3 shows an enlarged perspective view of the supporting structure for the first embodiment;

FIG. 4 shows an enlarged perspective view of the part rejection unit of the first embodiment;

DETAILED DESCRIPTION

The term "cap" as used in this description should be understood as any vessel or object comprising of a side wall and a bottom wall forming a cavity. The vessel or object may also comprise of a plurality of side walls and bottom walls.

Figure 1:
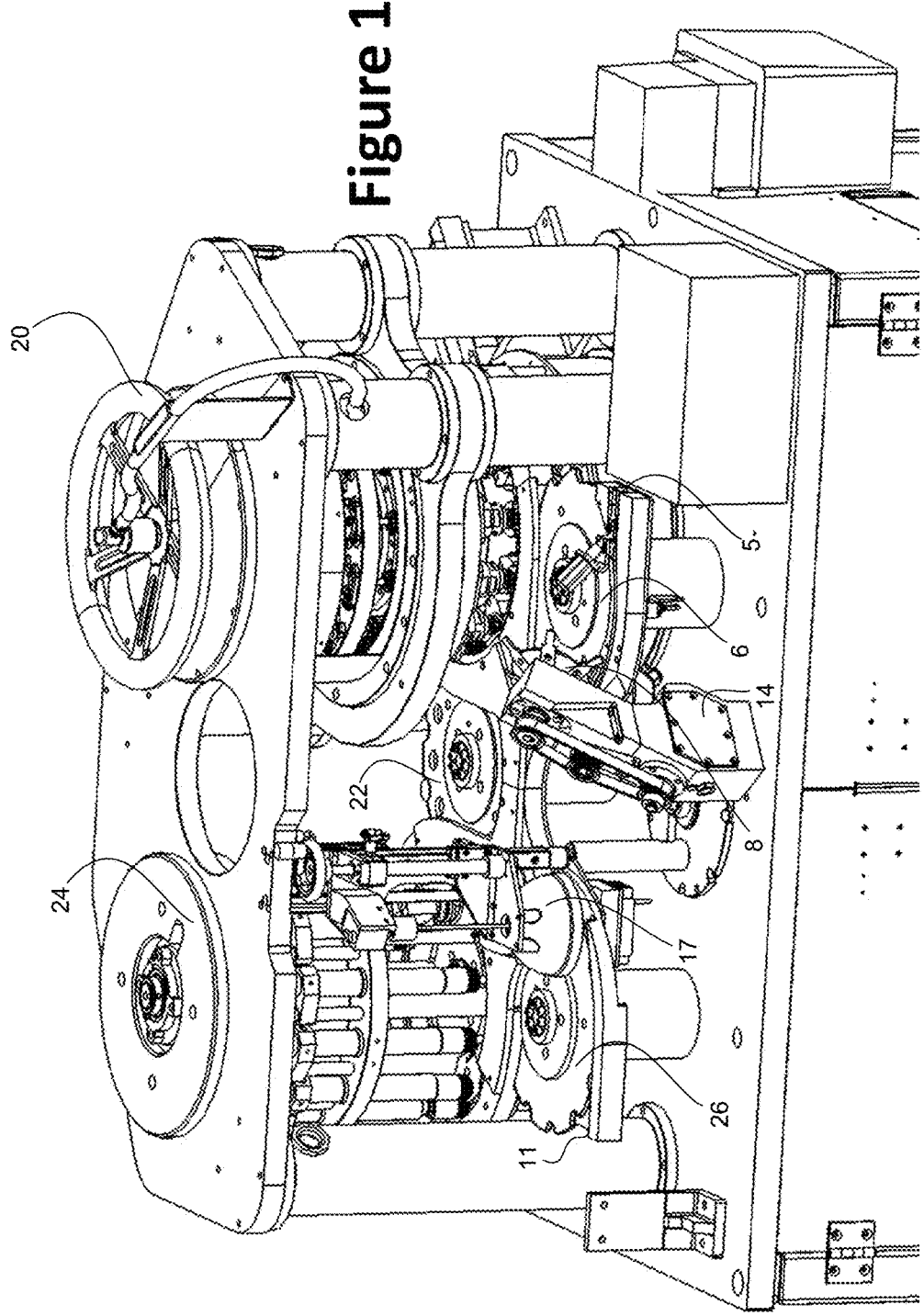
FIG. 1 shows an oblique view of a cap processing machine having a star-wheel receiving a line of caps, a frustoconical spark test wheel arranged on the star-wheel, a slitting turret receiving caps from the receiving star wheel, an intermediary pocket wheel receiving caps exiting the slitting turret, and a band folding turret receiving caps from the intermediary pocket wheel, an exit pocket wheel receiving caps from the band folding turret, and a vision inspection unit arranged to perform a machine vision inspection of the caps in the exit pocket wheel, with the incoming track of caps being aligned with the outgoing track of caps.

FIG. 1 illustrates an example of a context in which some of the embodiments described herein can find application. It will be appreciated that some embodiments herein are applicable to different apparatus. FIG. 1 shows a cap processing machine having a star-wheel 6 receiving a line of caps on a supply track 5, a frustoconical spark test wheel 8 arranged on the star-wheel 6, a slitting turret 20 receiving caps from the receiving star-wheel 6, an intermediary pocket wheel 22 receiving caps exiting the slitting turret 20, and a band folding turret 24 receiving caps from the intermediary pocket wheel 22, an exit pocket wheel 26 receiving caps from the band folding turret 24, and a vision inspection unit 17 arranged to perform a machine vision inspection of the caps in the exit pocket wheel 26. The incoming track 5 of caps is aligned with outgoing track 11. A rejection unit 12 is not shown in FIG. 1, and is to be arranged along the outgoing track 11, as illustrated in FIG. 4.

While the spark test wheel 8 is arranged on the receiving star wheel 6 in the embodiment of FIGS. 1 and 3, it will be appreciated that the spark test wheel 8 can alternatively be arranged on another pocket wheel of the conveyance system, such as intermediary pocket wheel 22 or exit pocket wheel 26 as desired.

Figure 2A:
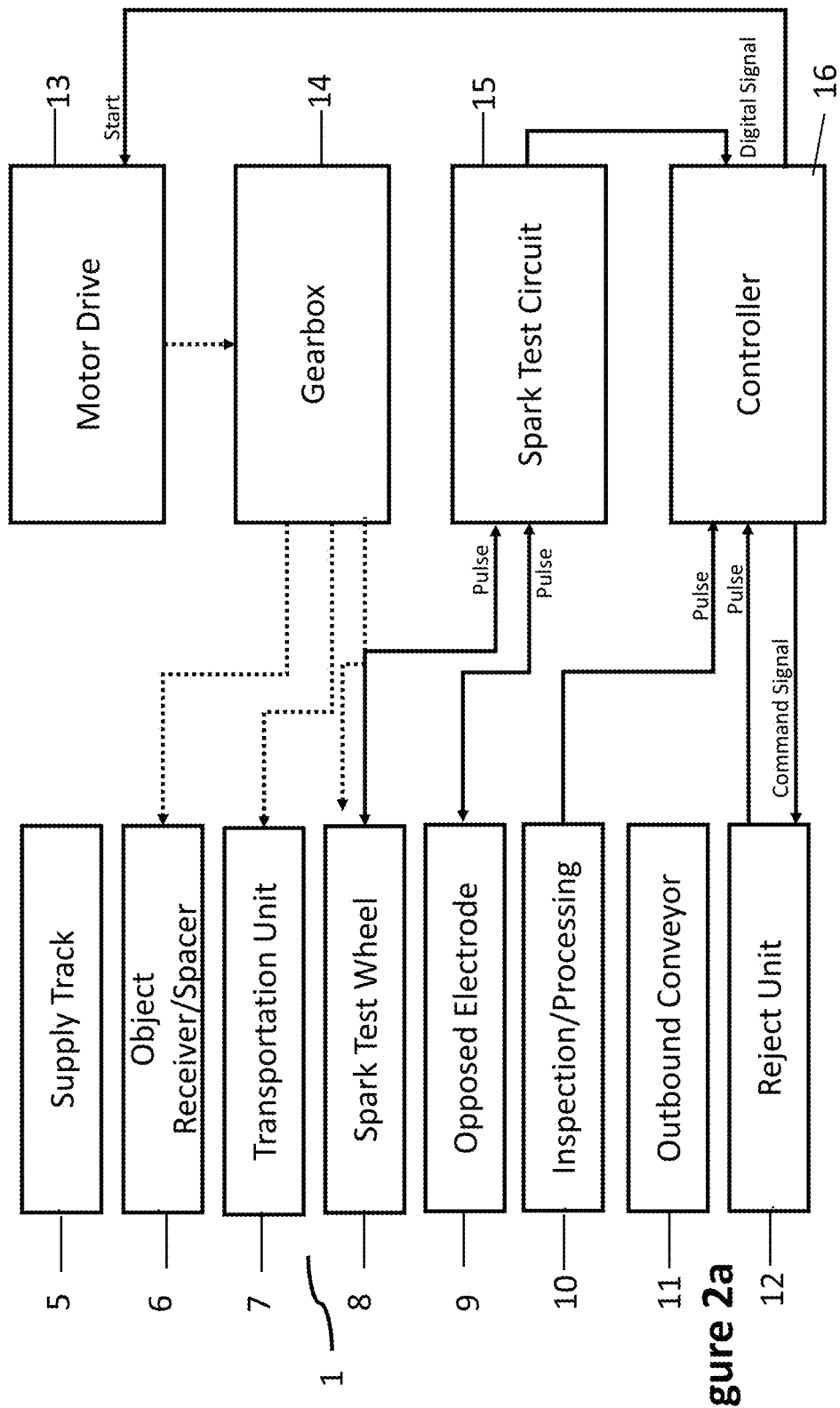
FIG. 2a shows a block diagram demonstrating the interactions between the various components of a first system having mechanically synchronized components.

FIG. 2a illustrates a schematic block diagram of a testing apparatus 1 and shows both the components contained in the apparatus 1 and their interactions. Each component of the apparatus 1 is described hereinafter.

Apparatus 1 comprises of a supply track 05, an object receiver 06, a transportation unit 7, a spark test wheel 8, an opposed electrode 9, inspection or processing station 10, an outbound conveyor 11 and a reject unit 12 as well as a motor drive 13, a gearbox 14, a spark test circuit 15 and a controller 16. The inspection or processing station or stations can comprise a variety of different components as desired. In the embodiment of FIG. 1, band slitting and folding operations are performed in addition to a machine vision inspection. It will be appreciated that such operations can vary from case to case.

Supply track 5 can be mechanical handling equipment moving products from one location to a destination. It can supply the apparatus 1 with caps 2 to be tested by the spark test wheel 8 and the opposed electrode 9. The automation process 10 can provide object processing or testing or a combination of the latter on the transportation unit 7. The supply track 5 can be embodied as an air track conveyor, a belt conveyor, a vacuum conveyor or any other mechanisms permitting the transportation of objects to be tested, typically with the objects conveyed one against the other in a single file manner.

Object receiver 6 is a mechanical device which receives the parts, namely in the example given, untested caps 2 provided by the supply track 5 and creates a predetermined physical position and spacing between the caps 2 on the conveyor or transportation unit 7. The physical spacing provides the necessary conditions for an accurate high voltage spark testing by the spark test wheel 8 accomplished by applying pressure on the bottom wall 4 of cap 2 without touching its side wall 3 and allows for a precise rejection of faulty caps 2b by reject unit 12. The object receiver 6 can be connected to the gearbox 14 and mechanically driven by motor drive 13. In one embodiment, the object receiver 6 is the entrance of a single circular rotating element containing cavities, further described below. In another embodiment, the object receiver 6 is a rotating worm gear (i.e. a helical drive). In a further embodiment, the object receiver 6 is a cleated belt containing a set number of cleats and spacing between them.

Transportation unit 7 is a mechanical device permitting the flow of the caps 2 through the apparatus 1 between the supply track 5 and the outbound conveyor 11. The transportation unit is connected to the gearbox 14 and is mechanically driven by motor drive 13. In one embodiment, the transportation unit 7 and the object receiver 6 is a single circular rotating element containing cavities receiving caps 2 in a one to one ratio with regards to the quantity of caps 2 per cavity, and transporting the caps 2 between the supply track 5 and the outbound conveyor 11 in a circular path. In another embodiment, the transportation unit 7 is a conveyor such as a belt conveyor, a vacuum conveyor or any other mechanisms permitting a linear transportation of objects.

Spark test wheel 8 in the embodiment of FIGS. 1, 3 and 4 has a shaped head and a plurality of probe fingers 8' attached to the head that each have active electrode tips, and alternatively it can be a made from single part of insulated material supporting the fingers 8' with active electrode tips. The spark test wheel 8 is connected to the gearbox 14 and is mechanically driven by the motor drive 13. The spark test wheel 8 accomplishes the spark test on caps 2 through an electrode situated at the end of every probe finger 8' of the spark test wheel 8, a high voltage source and a opposed electrode 9 located on or under the transportation unit 7 which detects a high voltage discharge should there be a micro-hole present in the cap 2 being tested.

Opposed electrode 9 is an electric component that serves as the secondary electrode in the spark test. When the object is free of any micro-hole or tear, then there is no path for the spark. However, when a breach in the insulator is found, a spark can travel. The spark is detected by the opposed electrode 9 which sends a signal to the spark test circuit 15. In this embodiment, the top of the electrode 9 is shaped in a circular fashion, but it can be appreciated that the shape can take a different form. The electrode 9 can also be electrically insulated from the supporting structure. In the embodiment where the transportation unit 7 is a single circular rotating element containing cavities, the opposed electrode 9 is located on a supporting structure and is positioned directly underneath the probe finger of the spark wheel 8 that possesses a longitudinal axis forming a perpendicular angle with the surface of the supporting structure. In another embodiment, the opposed electrode 9 is located in the transportation unit 7, either mounted on an opposed spark test wheel or as a stationary electrode.

The inspection/processing unit 10 can include, for example, a visual image recording device performing an optical test on the caps 2a. In one embodiment, the test conducted by the camera 10 is a color detecting test whereby a cap 2a which possesses a different color pigment from the other caps 2a is detected and is discriminated from the lot. In another embodiment, the camera 10 detects any physical impurities on the caps 2a. A cap 2a possessing impurities such as excess material, indents, and irregular size can be discriminated from the lot. Once the camera 10 detects a faulty cap 2b, a signal is sent to controller 16.

Outbound conveyor 11 is a mechanical handling equipment moving products from a location to a destination. It provides the transportation required by caps 2a to reach the reject unit 12 after being tested by the spark test wheel 8 and any other subsequent process at 10. The outbound conveyor 11 can be embodied as an air track conveyor, a belt conveyor, a vacuum conveyor or any other mechanisms permitting the transportation of objects.

Reject unit 12 can be a mechanical device containing a sensor which rejects any faulty caps 2b as detected by the spark test wheel 8, or any other test unit present on the apparatus 1. The reject unit 12 can communicate with the controller 16 by receiving command signals to reject faulty caps 2b and transmit the data collected by its sensor. In one embodiment, the reject unit 12 comprises an air nozzle which creates a local pressure increase through an air blast as a faulty cap 2b passes by. In another embodiment, the reject unit 12 comprises an electro-mechanical kicker or a pneumatic actuator positioned perpendicularly to the outbound conveyor 11 whenever the reject unit 12 receives the signal from controller 16 to remove a faulty cap 2b. In another embodiment, the reject unit 12 comprises a liquid-powered mechanism discharging a liquid jet, such as an aqueous liquid, through a nozzle positioned perpendicularly to the outbound conveyor 11 whenever the reject unit 12 receives the signal from controller 16 to remove a faulty cap 2b.

In some embodiments, the tracking (by timers, encoders or part sensors) of the passage of caps from inspection until arriving at the reject unit 12 can be handled with the help of a computer or a controller so that the specific part found to have a defect can be rejected. In the embodiment of FIG. 1, rotational encoders are used to detect the rotational position of the transport system 7 including the wheels and turrets. The exit conveyor 11 (see FIG. 4) can also have an encoder. These encoders are used to know the position of the caps 2 in the apparatus 1.

While the reject unit 12 can reject a single part when the mechanical response of the reject unit is quick enough and there is sufficient spacing between parts, the reject unit can be configured to reject multiple parts. For example, when a defective cap 2b is detected by the spark test or any other test on apparatus 1, the reject unit 12 can be activated to reject a number of caps 2a including the detected defective cap 2b. While this means that the number of caps 2a recycled is greater, this can simplify the operation of the reject unit 12 or eliminate the need for a significant spacing between caps 2a.

In some embodiments, the reject unit 12 includes a sensor for sensing the passage of a rejected cap 2b in chute 36. In the embodiment of FIG. 4, the reject unit 12 includes sensor 34 for detecting the presence of caps as they are conveyed on the outbound conveyor 11. If sensor 34 detects the presence of faulty cap 2b that has not been ejected in to reject chute 36 or that a good cap 2c is missing, then a signal is sent to controller 16 to alert the operator.

As known in the art of manufacturing caps, rejected caps 2b can be recycled.

Motor drive 13 is a mechanical system comprises a motor (which may be electric, pneumatic, or hydraulic) which provides the necessary torque for the apparatus 1 to function. In the embodiment presented in the block diagram of FIG. 2a, the motor drive 13 mechanically drives the object receiver 6, the transportation unit 7 and the spark test wheel 8 through gearbox 14. In another embodiment, the motor drive 13 is directly connected to the object receiver 6 and the transportation unit 7 while the spark test wheel 8 is driven through the gearbox 14. In another embodiment, the motor drive 13 is directly connected to the object receiver 6, the spark test wheel 8 is driven through the gearbox 14 and the transportation unit 7 is driven by a motor drive external to apparatus 1.

Gearbox 14 can be a transmission system containing gears which modifies the rotational drive provided by the shaft of the motor drive 13. The gearbox 14 ensures the synchronization of the object receiver 6, the transportation unit 7 and the spark test wheel 8. Alternatively, the rotation synchronization can be ensured mechanically by using timing belts. This synchronization allows for the spark test probe fingers 8' of the spark test wheel 8 to avoid contacting the side wall 3 of the cap 2 being tested. This improves stability of the object handling during testing and reduces the risks of damaging the cap. Also, the synchronization allows the transportation unit 7 and probe finger 8' speed to match such that contact between the electrode situated on the end of the probe finger 8' and the bottom of the cap 2 can be made with a reduction in the separation between the high voltage electrodes without disturbing the high speed conveyance of the caps 2 being tested. In one embodiment, the transportation unit 7 and the object receiver 6 is a single circular rotating element containing, for example, twelve cavities which is directly connected to the motor drive 13. The spark test wheel 8 contains, for example, six probe fingers and is mechanically driven by the motor drive 13 through the gearbox 14. In this embodiment, the gearbox 14 comprises of gears permitting a 1:2 conversion of the rotational drive provided by the motor drive 13. The number of cavities and probe fingers need not be a multiple of one another. The number of cavities and fingers can be any desired number that suits the geometry and dimensions of the installation. Thus, the ratio of the number of probe fingers to pocket wheel cavities can typically be from about 2:3 to 1:4, although a ratio close to 1:2 has been found to be effective and compact. In another embodiment, the object receiver is a worm which is connected to the gearbox 14 and the spark test wheel 8 contains a set amount of probe fingers which is connected to the gearbox 14. In this embodiment, since the worm gear performs six turns for every one turn accomplished by the spark test wheel 8, the gearbox 14 comprises of gears that permits a 6:1 conversion of the rotational drive provided by the motor drive 13.

Spark test circuit 15 can be an electronic circuit, known in the art, to detect a high voltage discharge passing through a faulty cap 2b, thus exposing the presence of a micro-hole or micro-tear. The voltage used can be direct current or suitable alternating current and is typically in the kV range. The spark test circuit 15 can be physically situated near the spark test wheel 8 and connected to the primary electrodes of the spark test wheel 8 and the opposed electrode 9 positioned on or under the transportation unit 7. Once the detection is accomplished, the spark test circuit 15 sends a signal to the controller 16 communicating the presence of the faulty cap 2b.

Controller 16 performs receptive, comparative and corrective functions. The controller 16 receives electrical signals from the spark test circuit 15 pertaining to the presence of faulty caps 2b as well as electronic signals from the reject unit 12 which may contains a sensor monitoring the caps 2b being ejected from the outbound conveyor 11. In one embodiment, the controller 16 tracks faulty caps 2b using timing thereby sending a command signal to reject unit 12 to reject the upcoming faulty cap 2b after a set amount of time has elapsed after it was detected by the spark test wheel 8. In another embodiment, the controller 16 tracks faulty caps 2b based on location thereby sending a command signal to reject unit 12 to reject the upcoming faulty cap 2b following the passing of a set amount of caps 2a (by interpreting encoder signals) after it was detected by either the spark test circuit 15. The controller 16 can also send a signal to the motor drive 13 to start or stop the testing process supported by apparatus 1.

Figure 2B:
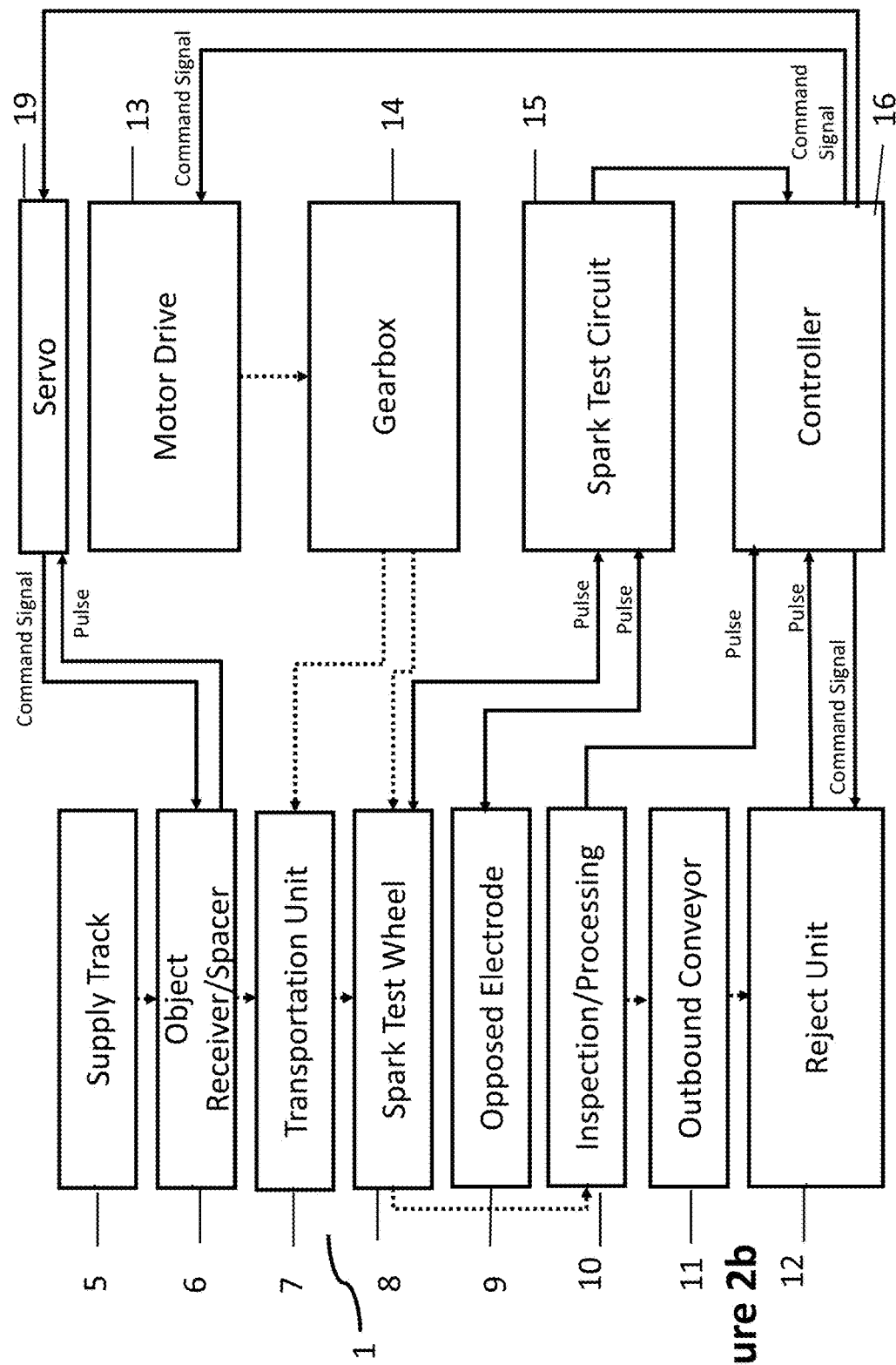
FIG. 2b illustrates a block diagram of a second system where the synchronization is accomplished with an electronic part synchronization.

FIG. 2b illustrates a block diagram of apparatus 1 where the synchronization is accomplished with an electronic component (i.e. a servo supply system) and comprises both the components contained in the apparatus 1 and their interactions. The supply track 5, object receiver 6, transportation unit 7, the spark test wheel 8, the controller 16 and a servo 19 of the apparatus 1 are described hereinafter.

Object receiver 6 is, in this embodiment, an electronic control system monitoring the flow of caps 2 from the supply track 5 onto the transportation unit 7 through an object detector (e.g. an infrared detector), which detects the presence of caps 2, and the servo 19 which conducts corrective measures. The object receiver 6 uses a stop-and-go technique to create spacing between caps 2 as they enter the transportation unit 7. Such a stop-and-go system can be practical for linear conveyors systems, such as in the embodiment of FIG. 5.

The object receiver 6 is thus electronically synchronized with the transportation unit 7 and the spark test wheel 8. This is accomplished by the controller 16 which controls both the motor drive 13 which drives the transportation unit 7 and spark test wheel 8 through the gearbox 14 and the servo 19 which controls the object receiver 6.

It will generally be appreciated that synchronization between the transportation unit 7 and the spark test wheel 8 can also be achieved by electronic synchronization using position encoders and motor controllers. Optionally, the opposed electrode 9, if motorized, can be synchronized using position encoders and a motor controller.

Transportation unit 7 can be a mechanical device causing the flow of the caps 2 through the apparatus 1 between the supply track 5 and the outbound conveyor 11. The transportation unit 7 is driven by the motor drive 13 through the gearbox 14 and possesses an operating speed that is synchronous with the spark test wheel 8 and the object receiver 6.

Servo 19 can be an electronic device which automatically corrects the performance of a mechanism. The servo 19 receives signals from the controller 16 to determine the required correction in order for the caps 2 to have the proper spacing on the transportation unit 7 after they leave the supply track 5.

In the embodiment of FIG. 1, the supply track 5 may comprise an air track which uses jets of high velocity air generated by a constant positive back pressure to move the caps 2 through guides.

The caps 2 are introduced into the air column track either directly through the exit conveyor of the production area or by the unloading of crates containing caps 2. The guides ensure that the caps 2 are properly lined up one after the other, forming a long queue that is propelled forward.

In this present embodiment, the object receiver 6 and the transportation unit 7 are present on a single rotating element, namely a starwheel, described hereinafter.

Starwheel 6 comprises a star-shaped rotating central element made out of insulated material, possessing a plurality of evenly spaced J shaped (saw toothed) cavities in the central disk, each cavity allowing a smooth angle of entry.

In this embodiment, the star wheel 6 is driven directly by the gearbox 14, allowing it to move synchronously with the spark test wheel 8. In this present embodiment, there are twelve cavities spread evenly over the circumference of the star-shaped rotating central element.

The physical separation occurs when the caps 2 enter the star wheel 6 at a predetermined ingress rate, for example over thousands caps per minute, by being clipped by the smooth edge of the cavities. The caps 2 then follow the circular movement of the starwheel 6 at constant speed to be tested by the spark test wheel 8 and exit through the outbound conveyor 11.

In this present embodiment, the spark test wheel 8 comprises a frustoconical module, a plurality of probe fingers each possessing an electrode, and a support module mounted as shown in FIGS. 1 and 3 to the base that is common with other components.

The frustoconical module is a rotating element, upon which probe fingers are mounted. In this embodiment, the frustoconical module 8 is driven by motor drive 13 through gearbox 14 so that the module 8 rotates at exactly twice the speed as the wheel 6. The mechanism permitting the synchronization of the object receiver 6, spark test wheel 8, the transportation unit 7 is described hereinafter.

Probe fingers can be conductive members terminating in electrode tips as illustrated in FIG. 3. Alternatively, the fingers can be made out of an insulating material which provides physical support for electrodes connected by a wire to the high voltage source. When the fingers are insulated except for their tips, it may be possible to have a starwheel made of a conductive material. A person skilled in the art will understand the need to prevent providing a path for a spark from the electrode using suitable gaps or insulation. As also illustrated in FIG. 3, the probe fingers are arranged to contact with a desired amount of force the bottom wall 4 of the caps 2 to allow for a more accurate spark test by reducing the distance between electrode and opposed electrode 9 during the testing of a cap 2. Furthermore, the testing is accomplished without touching the sidewall 3 of the cap 2 which lowers the risk of jamming or ejection in the transportation unit 7 at high speeds. This advantageous configuration also allows for the use of a lower value of high voltage than typically employed in spark tests and/or for a desired high voltage level to be more effective, thus improving the efficiency and/or quality of the spark test at high speed. In this embodiment, the probe fingers are shown as being components separate from the frustoconical module to which they are attached. In another embodiment, the probe fingers and the electrodes can be extensions from the frustoconical module thus forming a single conductive probe member.

The spark test wheel 8 has a frustoconical shape in the embodiment of FIGS. 1 and 3 because this allows the fingers 8' that terminate in active electrodes to follow the circular path of transportation unit 7. If the diameter of the wheel 6 is large enough, effective finger movement can be provided by a planar arrangement of fingers instead of a conical arrangement without increasing the risk of contact with sidewalls 3. The angle of the fingers with respect to the axis of rotation of the wheel 8 is chosen to match the diameter of the circular path of unit 7. A relatively small wheel 6 with 12 pockets is an example of compact arrangement that efficiently handles caps at high speed.

The electrodes at the end of the fingers 8' are the primary electrode in the spark test. The electrodes are connected to a source of high voltage, typically 5 to 20 kV, which is part of the spark test circuit 15. The supply of the high voltage can be pulsed, for example in synchronization with the position of the electrode, or a continuous supply. When the object is free of any micro-hole or tear, then there is no path for the spark. However, when a breach in the insulator is found, a spark can travel. The high-voltage supply circuit can limit the flow of current so that little power is provided to the spark, so as to avoid damaging the electrodes and 9 and consuming power needlessly. In this embodiment, the bottom of the electrode is shaped in a circular fashion, but it can be appreciated that the shape can take a different form. The electrodes can also be electrically insulated from the probe fingers and the base frustoconical module.

The support module shown in FIGS. 1 and 3 is an immovable component which provides rotatable bearing support to the frustoconical module as well as the probe fingers and can also contain the spark test circuit 15.

A timing belt, connected to gearbox 14, drives a toothed pulley 18 to turn frustoconical module. The timing belt can be made of rubber and provide insulation between the spark test wheel 8 and the motor drive 13, should the insulation not be within the spark test wheel 8. Alternatively, the casing 14 can be insulated and protect the gears from any passage, transfer or leakage of electricity. It also has a connection (not shown) to motor drive 13 which provides necessary torque for the operation of the process enabled by the apparatus 1.

The frustoconical module rotates in the same direction as starwheel 6 in a tilted fashion to follow the horizontal circular path of the cavities of starwheel 6. The rotation of frustoconical module is provided by the motor drive 13 through gearbox 14. The advantageous configuration of having the motor drive 13 providing rotation to both the starwheel 6 and frustoconical module allows for the synchronization of both components. In this present embodiment, there are six probe fingers on the spark test wheel 8, which translates into a 1:2 ratio to the amount of cavities in the starwheel 6. The gearbox 14 comprises of gears permitting the 1:2 conversion of the rotational drive provided by the motor drive 13. The gear ratio can also be achieved by selecting the relative sizes of the toothed pulley 18 and its driving module of the motor drive 13 (see FIGS. 1 and 3).

The synchronization of the starwheel 6 and frustoconical module 8 permits the probe fingers to conduct the spark testing without touching the caps 2 side wall 3. As the starwheel 6 rotates, it transports caps 2 along a circular path. The frustoconical module 8, rotating synchronously to starwheel 6, is calibrated in such a way that a probe finger is constantly directly above a cavity, the longitudinal axis of the probe finger forming a perpendicular angle with the instantaneous direction of the cavity. This advantageous configuration does allow the probe finger to apply pressure on the bottom of the container 2 thereby minimizing the gap between electrode and opposed electrode 9.

Once the probe finger is in the position aforementioned, the electrode situated on the probe finger can discharge a high voltage pulse. If a micro-hole is present in the cap 2, the high voltage pulse travels through the micro-hole and the current of the pulse is detected in spark test circuit 15.

Once the aforementioned detection is accomplished, the spark test circuit 15 sends a signal to controller 16 pertaining to the detection of a faulty cap 2b. If no micro-hole is present, the high voltage pulse at electrode does not create a current reading in the spark test circuit 15.

In this present embodiment, once the caps 2 pass through the spark test wheel 8, the caps 2a exit the starwheel 6 and enter the next wheel, and in FIG. 1 this would be the turret wheel of unit 20. In other embodiments, the number of wheels after the wheel 6 may vary and can be optional. The caps 2a exit the wheel 26 and slide onto the outbound conveyor 11.

In the embodiment of FIG. 1, the transportation unit 7 is arranged to have the outbound conveyor 11 in line with the inbound conveyor 5. It will be appreciated that the direction of the flow of caps 2 can be changed by the apparatus 1 as desired by varying the number of wheels and the exit path.

Manufacturing steps other than those described with reference to FIG. 1 can be performed on caps 2.

In the embodiment of FIG. 1, gearbox 14 is a mechanical system comprising of an insulated casing, a set of gears and a gearbox driving module. Gearbox 14 is connected to the motor drive 13 from which it draws torque and transmits it to other components of apparatus 1. In this embodiment, the gearbox 14 is only connected to the spark test wheel 8. In other embodiment, a different size starwheel 6 or the pocket wheel 26 is also connected to ensure synchronous rotation.

As shown in FIG. 4, the outbound conveyor 11 can comprise conveyor belts 11a and a slit 11b connected to a vacuum fan or pump. The outbound conveyor 11 can be driven by a motor drive 13 external to apparatus 1 at the linear speed corresponding to the tangential speed associated with the starwheel 6 rotation.

In this present example, the outbound conveyor 11 can comprise two equal lengths conveyor belts 11a that are spaced by a predetermined distance and runs in a parallel manner in the same direction. As assembled, the conveyor belts permit the transportation of the caps 2a from the exit of the transportation unit 7 to their final destination, passing by the reject unit 12.

The vacuum can provide a local pressure drop by sucking out the surrounding air thereby causing the caps 2a to maintain a higher contact pressure with the conveyors belts. The vacuum drawing air through spacing permits the caps 2a to resist external forces such as vibration from the apparatus, naturally occurring airstreams and variations in the speed of outbound vacuum track that normally would overcome the static friction between the caps 2a and the conveyor belts. The belt could alternatively be a single perforated belt or comprise a number of belts with a plurality of slits.

FIG. 3 illustrates the various components forming the supporting structure as embodied in the first embodiment of apparatus 1. The supporting structure is the mechanical component which houses some major components contained in the apparatus 1. In this present embodiment, the supporting structure 21 provides support to the starwheel 6.

The supporting structure comprises of circular side wall and a bottom plate, forming a circular hollow containing the circular components of the first embodiment of apparatus 1. The caps 2 move in a circular fashion alongside the circular side wall, the moving force being provided by the edge of the cavities of starwheel 6. Additional circular hollows formed by circular side wall and the bottom plate containing additional pocket wheels or additional turrets can be arranged as desired when room is required for testing purposes or additional manufacturing operations are integrated.

Opposed electrode 9 serves as the secondary electrode in the spark test. The electrode 9 is located on the supporting support and is be positioned under a primary electrode, situated on the spark test wheel 8, in such a way that its center axis is aligned with the center axis of the primary electrode.

In another embodiment, the opposed electrode 9 can be a stationary electrode mounted on the supporting surface on which the caps 2 slide while transported by a bottom plate embodied as a bottom wheel, turning at the same speed as the starwheel 6. During testing, the primary electrode on the probe fingers makes contact with the bottom wall 4 of the caps 2, while the bottom wheel keeps the caps 2 moving in spite of any frictional force caused by the pressure of the probe fingers pushing the bottom of the caps 2 against the stationary supporting surface where the opposed electrode 9 is found. Alternatively, the bottom wheel can be a bottom support disk in which an opposed electrode 9 is positioned under each cavity. Such electrodes can be connected together if desired. In another embodiment, the bottom wheel is a conductive plate situated under the starwheel 6 and connected to the spark test circuit 15, thus assuming the function of opposed electrode 9.

As illustrated in FIG. 3, during the testing of a cap 2, the bottom wall 4 is situated between the electrode of the finger 8' and opposed electrode 9. Pressure is applied on the bottom wall 4 by the probe finger, thus narrowing the physical gap between the two aforementioned electrodes and leading to a more efficient spark test. The amount of pressure exerted can be adjusted through mechanical adjustments, for example a height adjustment mechanism within support module 14, such a shim plates. In one embodiment, the size of the probe fingers 8' can be modified to provide efficient pressure application on the bottom wall 4. In another embodiment, the frustoconical module 8 can be modified to achieve a similar goal. Adjustments can be with regards to the tilt of the frustoconical module, in relation to the supporting structure, the angle between the probe fingers 8' and the rotational axis of the frustoconical module 8, the spatial positioning of the frustoconical module 8 or the physical size of the frustoconical module 8.

FIG. 4 illustrates the various components forming the reject unit 12. In this embodiment, the reject unit 12 comprises an air nozzle 30 supplied with air through an electrically controlled valve 32 to propel a cap 2b into a reject object chute 36. The actuation of the valve 32 can be controlled by the controller 16 having received an indication of the defective cap from spark test circuit 15 or another inspection unit 10.

A sensor 34 is provided on the conveyor 11 to detect that the defective cap 2b was indeed removed from the conveyor 11. Sensor 34 is connected to controller 16. If the sensor 34 indicated that the cap 2b has not been ejected, an operator alert signal can be generated by controller 16.

In this embodiment, once the caps 2a leave the transportation unit 7, the caps 2a enter the outbound conveyor 11 and are transported in front of the reject device 12 which rejects any faulty caps. Non-faulty caps move on to the packaging unit or a storage container or any other subsequent upstream process.

In another embodiment, the controller 16 uses an alternative method to determine the presence of the faulty cap that is less precise. The reject device 12 thus receives a signal to eliminate a subset of caps which includes the faulty cap. Though less efficient than the previous examples, this embodiment still ensures that faulty caps are not released into the output of good quality product.

In the present embodiment, the reject mechanism 12 is an air jet 30 in the form of an air gun with its nozzle positioned perpendicularly to the outbound conveyor 11. The reject mechanism 12 receives the signal to blast air toward the caps 2b on the outbound conveyor 11 from controller 16.

Alternatively, an additional release mechanism may be added to the reject device 12 at the bottom of the outbound conveyor 11 pointing upward toward the lower flat part of caps 2 at a predetermined angle, for example 45 degrees. The additional release mechanism is synchronized with the reject mechanism 12 and provides a local pressure increase in the form of an air jet whenever a faulty cap appears in front the reject device 30. This allows the faulty cap to overcome its static friction with the outbound conveyor 11 more easily.

In another embodiment, the reject mechanism 12 is a plunger or pushing mechanism with an extendable arm which extends its arm whenever the reject mechanism 12 receives the signal from controller 16 to remove a faulty cap from the outbound conveyor 11.

Figure 5:
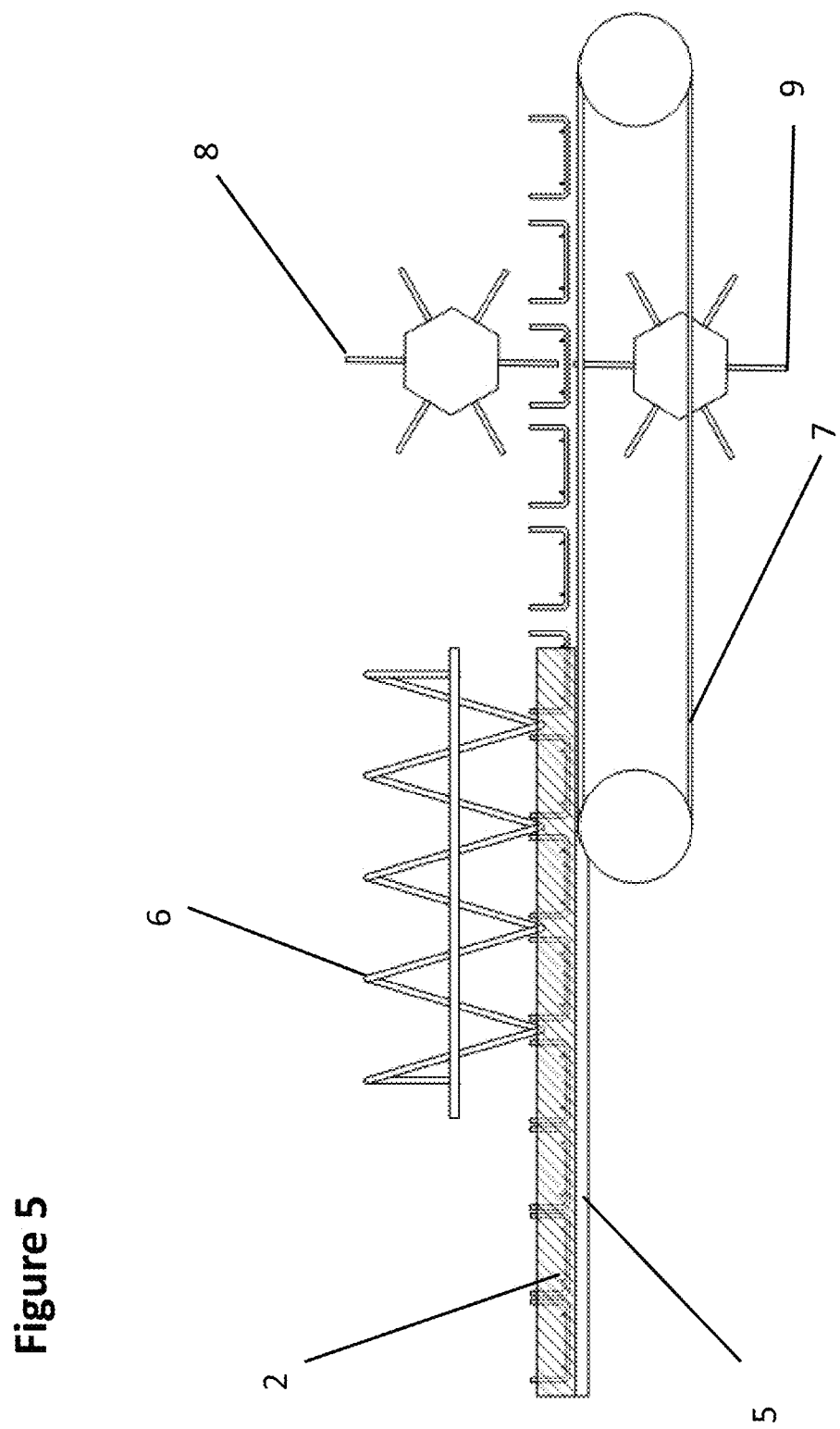
FIG. 5 shows a schematic side view of a second embodiment using a linear conveyance and flat spark test wheel.

FIG. 5 illustrates the various mechanical components forming the second embodiment of apparatus 1 in which the reject unit 12 similar to the first embodiment of apparatus 1 is not illustrated.

In this present embodiment, the apparatus 1 comprises ten major components: a supply track 5, an object receiver 6, a transportation unit 7, a planar spark test wheel 8, an opposed spark test wheel 9 with mounted opposed electrodes, a motor drive, a gearbox, a spark test circuit and a controller. The motor drive, gearbox, spark test circuit and controller are not illustrated in the FIG. 5 for simplicity reasons. The second embodiment of the apparatus 1 follows a linear configuration to conduct the spark testing of caps. Each component of the second embodiment of apparatus 1 is described hereinafter.

In this present embodiment, the supply track 5, similar to the embodiment of FIG. 1, comprises an air track column which uses streams of high velocity air generated by a constant positive back pressure to move the caps 2, positioned one after the other to create a single file queue of objects pressed against each other. The supply track 5 is positioned to feed the entrance of the transportation unit 7, thus allowing the caps 2 to gently transfer from one mechanical handing equipment to the other.

In this embodiment, the supply track 5 has side walls that are lower than the tops of the caps 2 to allow for the thread or blade of a worm or spiral member 6 to engage the caps 2 while they are retained at the sides by guides (not illustrated).

In this embodiment, the object receiver 6 is a worm containing a thread of continuous thickness in the form of a helix. The pitch of the threads corresponds to a small amount more than the diameter of the caps 2 and the thickness of the threads allows for a separation of the caps 2. In this present example, the worm 6 contains four turns of the thread. In another embodiment, the worm 6 can have a blade whose thickness increases from ingress to egress, while maintaining the same pitch or distance between each turn of the blade. In this way, the blade can be thin when initially separating the caps 2, and the spacing between caps 2 leaving the worm 6 can be as desired.

The transportation unit 7 receives the spaced caps 2 in the position set by the worm 6. Transportation unit 7 can be a pair of belts separated by a gap or slit through which air is aspirated using a suction fan or pump (similar to the conveyor 11 of FIG. 4) that is synchronously driven along with the worm 6 and the two opposing spark wheels 8 and 9 by motor drive through gearbox. In another embodiment, the transportation unit 7 can also have a slotted belt, cleated belt or the like, and the use of suction can be option whether through a gap or slit or whether through perforations in the belt.

In this embodiment, the planar spark test wheel 8 is configured in the similar fashion as the spark test wheel 8 described in the embodiment 1 of apparatus 1.

In this present embodiment, the opposed spark test wheel 9 is made out of similar construction as spark test wheel 8, namely provided with probe fingers mounted with electrodes. In this case, opposed electrodes 9 are installed on the probe fingers of an opposed spark test wheel. In another embodiment, opposed spark test wheel 9 can be a smooth rim wheel with electrodes mounted on its surface and rotates synchronously with the object receiver 6, transportation unit 7 and spark test wheel 8.

The advantageous configuration described above allows for an efficient spark test at high speed. Similar to embodiment 1, the probe fingers and their rotation are configured in such a way as to only come in contact with the inside of the bottom wall 4 of the cap 2 being tested. Opposed spark test wheel 9 is configured in such a way that an opposed electrode is situated directly underneath a probe finger whenever a cap 2 is being tested. As such, the two electrodes pinch the bottom of the cap 2 for a very short amount of time, thus avoiding the friction usually generated due to a stationary secondary electrode. Hence, there is little chance for cap 2 to be disturbed from its conveyance path on the transportation unit 7.

In one embodiment, the opposed electrode can be a stationary electrode integrated into the conveyor 7, in the slot between the belts.

In an embodiment where the caps 2 have their inside cavity surface downwardly arranged on the transportation unit 7, the spark test wheel 8 can be arranged under the belt conveyor 7 to inspect the caps 2 from below. While a static second high voltage opposed electrode can be used, it is possible to arrange for the opposed second electrode to be a synchronized opposed spark test wheel 9 as well.

In one embodiment, the object receiver 6 is a cleated belt running above or a pair of cleated belts running along the sides of the supply track 5, with the caps 2 coming in between cleats that fix the position of the caps 2 and set a fixed spacing there between. The distance between the two cleats corresponds to at least the diameter of the caps 2. In this embodiment, the object receiver 6, the transportation unit 7 and the spark test wheel 8 operate synchronously to ensure an accurate high voltage spark test accomplished by reducing the distance between the finger probes 8' and opposed electrode 9 and without touching the cap 2 side wall 3. In another embodiment, the cleated belt assumes the function of both the transportation unit 7 and the object receiver 6, whereby the cleats are used to push the caps 2 forward through the spark test wheel 8.

What is claimed is:

1. A spark test apparatus comprising:
   a pocket wheel arranged to transport objects, each one of said objects having a cavity defined by a sidewall and bottom wall, in pockets of said pocket wheel; and
   a spark test wheel having probe fingers extending at an angle from an axis of rotation of said spark test wheel, said spark test wheel having a frustoconical arrangement and being mounted with respect to said pocket wheel to allow said probe fingers to move into and out of said cavities of said objects held within said pockets as said pocket wheel rotates.

2. The apparatus as defined in claim 1, wherein said pocket wheel is a star wheel arranged to receive from a supply conveyor a single-file line of said objects and to arrange said objects in pockets of said star wheel.

3. The apparatus as defined in claim 1, further comprising a motor drive connected to said spark test wheel, said motor drive being synchronized with a motor drive of said pocket wheel, said spark test wheel being arranged to allow said probe fingers to move into and out of said cavities of said objects without contacting said sidewalls of said objects.

4. The apparatus as defined in claim 1, wherein said spark test wheel is rotated by contact with said sidewalls of said objects.

5. The apparatus as defined in claim 1, wherein said spark test wheel is arranged to contact said bottom wall of said objects.

6. The apparatus as defined in claim 1, wherein said spark test wheel is driven by an electrically insulating mechanical coupling.

7. The apparatus as defined in claim 1, further comprising at least one further pocket wheel coupled with said star wheel for extending said transportation unit for providing either space for additional processing or testing of said objects or for providing a desired outlet direction.

8. The apparatus as defined in claim 3, wherein said synchronized drive comprises a single motor drive with at least one gearing for driving said pocket wheel and said spark test wheel in synchronization.

9. The apparatus as defined in claim 1, further comprising a reject unit associated with either said pocket wheel or a downstream outbound conveyor for rejecting ones of said objects having failed a spark test.

10. The apparatus as defined in claim 9, wherein said reject unit is configured to eject from either said pocket wheel or said downstream outbound conveyor a single one of said objects having failed a spark test.

11. The apparatus as defined in claim 9, wherein said reject unit is configured to detect the passage of said objects.

12. The apparatus as defined in claim 9, wherein said reject unit is configured to confirm that the single one of said objects having failed its spark test is accurately ejected from either said pocket wheel or said downstream outbound conveyor.

13. The apparatus as defined in claim 9, wherein said reject unit comprises at least one controllable fluid jet for propelling said objects from either said pocket wheel or said downstream outbound conveyor into a recycle path.

14. The apparatus as defined in claim 1, further comprising a spark test circuit connected to said spark test wheel.

15. The apparatus as defined in claim 14, further comprising a controller connected to said synchronized drive and said spark test circuit for generating a signal when one of said objects fails a spark test conducted using said spark test wheel.

16. The apparatus as defined in claim 1, wherein said objects comprise plastic caps and said probe fingers of said spark test wheel are arranged to rotate in and out of a cavity of said caps without contacting a side wall of said caps.

17. The apparatus as defined in claim 16, wherein said synchronized drive operates to inspect said caps at a rate greater than 2000 caps per minute.

18. A method of manufacturing a product, the method comprising:
   providing an inspection apparatus as defined in claim 1;
   providing plastic objects to be tested that are to form part or all of said product;
   using said spark test wheel to perform a spark test on said objects;
   rejecting ones of said objects having failed said spark test;
   using a remainder of said objects for said product.

19. The method as defined in claim 18, wherein said product is plastic container caps.

* * * * *